(12) United States Patent
Parce

(10) Patent No.: US 6,366,924 B1
(45) Date of Patent: *Apr. 2, 2002

(54) DISTRIBUTED DATABASE FOR ANALYTICAL INSTRUMENTS

(75) Inventor: J. Wallace Parce, Palo Alto, CA (US)

(73) Assignee: Caliper Technologies Corp., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/123,022

(22) Filed: Jul. 27, 1998

(51) Int. Cl.[7] .......................... G06F 17/30; G01N 35/00; E21B 49/00
(52) U.S. Cl. .......................... 707/104; 702/50; 702/31; 702/32; 422/68.1; 422/62
(58) Field of Search .......................... 707/104; 422/50, 422/62, 67, 68.1; 702/50, 31, 32

(56) References Cited

U.S. PATENT DOCUMENTS

| | | | |
|---|---|---|---|
| 4,831,582 A | 5/1989 | Miller et al. ................. | 364/900 |
| 4,947,355 A | 8/1990 | Koeman ................. | 364/571.01 |
| 4,958,283 A | 9/1990 | Tawara et al. .......... | 364/413.13 |
| 4,982,325 A | 1/1991 | Tignor et al. ................. | 364/200 |
| 5,131,272 A | 7/1992 | Minei et al. ................... | 73/431 |
| 5,265,247 A | 11/1993 | Wienck et al. .............. | 395/600 |
| 5,301,336 A | 4/1994 | Kodosky et al. ............ | 395/800 |
| 5,392,226 A | 2/1995 | Hamilton ................ | 364/551.01 |
| 5,437,838 A | 8/1995 | DeMornaville et al. ...... | 395/422 |
| 5,551,021 A | 8/1996 | Harada et al. .............. | 395/600 |
| 5,551,022 A | 8/1996 | Tariq et al. .................. | 395/600 |
| 5,555,505 A | 9/1996 | Oosawa et al. ......... | 364/470.07 |
| 5,631,844 A | 5/1997 | Margrey et al. ............. | 364/496 |
| 5,699,157 A | 12/1997 | Parce .......................... | 356/344 |
| 5,730,124 A | 3/1998 | Yamauchi .................... | 128/630 |
| 5,732,277 A | 3/1998 | Kodosky et al. ............. | 395/800 |
| 5,740,801 A | 4/1998 | Branson ................... | 128/653.1 |
| 5,810,657 A | 9/1998 | Pariseau ....................... | 454/61 |
| 5,842,787 A | 12/1998 | Kopof-Sill et al. .......... | 366/340 |
| 5,869,004 A | 2/1999 | Parce et al. .................. | 422/100 |
| 5,876,675 A | 3/1999 | Kennedy ...................... | 422/99 |

FOREIGN PATENT DOCUMENTS

| | | | |
|---|---|---|---|
| GB | 2 248 696 | * | 4/1992 |
| GB | 2251321 A | * | 7/1992 |

\* cited by examiner

*Primary Examiner*—Jack Choules
(74) *Attorney, Agent, or Firm*—Ritter, Lang & Kaplan LLP

(57) ABSTRACT

A method is provided for displaying chromatographic data using a graphical user interface. This method is preferably implemented as a software package which takes chromatographic data generated by varying fluorescence levels in a sample.

27 Claims, 6 Drawing Sheets

DISTRIBUTED DATABASE FOR ANALYTICAL INSTRUMENTS

BACKGROUND OF THE INVENTION

Embodiments of present invention relate to a method and apparatus for the sharing of test parameters and data from analytical instrumentation. More particularly, the present invention provides for the storage and retrieval of operating parameters for analytical instruments and the data generated thereby using a database accessible over a network.

Typically, the analysis of samples using an analytical instrument normally requires the operator to set operating parameters of the analytical instrument prior to performing the experiment at hand. The test is then performed, generating experimental data which may then be interpreted. In the area of biochemical analysis, the instrument's set of operating parameters is known as a "protocol," and includes all the relevant information necessary for the instrument to complete the analysis. A protocol may include a large number of parameters. Thus, the instrument's operator faces the daunting task of correctly entering each parameter of the requisite protocol.

This can be especially troublesome when an operator at one location attempts to replicate a test previously performed at another location. Not only must the protocol be correctly entered, the operator must somehow acquire the data from the remote location in order to make a comparison of the original test data and that generated by the present test. Moreover, information unrelated to the operation of the analytical instrument, but often necessary nonetheless, is frequently unavailable, incompletely, or inaccurately recorded. Such information might include operator identification, time, and date of the test, model, and revision of instrument used, and other such information.

In addition, most research facilities normally support a number of analytical instruments for performing all manner of analyses. Determining when (or even if) a comparable test has been run can easily become problematic. This is especially true when multiple research facilities are being supported. Currently, a person wishing to determine such information is consigned to manually reviewing records in an effort to find comparable experiments and/or experimental data.

What is therefore needed is a method for setting the analytical instrument's parameters and recording data generated thereby that can be easily accessed and searched. Moreover, such an application should support searching of the parameters and data stored therein. Preferably, such a system should be able to carry out these operations remotely.

SUMMARY OF THE INVENTION

It is a general object of the present invention to provide methods and processes that provide for the storage and retrieval of test parameters (e.g., the analytical instrument's operational settings) and test data (e.g., as acquired from an analytical instrument). More particularly, the present invention provides for the storage and retrieval of operating parameters for analytical instruments and the data generated thereby using a database accessible over a network.

In one embodiment of the present invention, a method of operating an analytical instrument is described. The analytical instrument will have one or more wells for holding samples, buffers, and the like. First, configuration information is stored into the database. The configuration information includes step configuration information representing at least one step performed in executing the test to be performed by the analytical instrument. The step configuration information, in turn, includes information regarding the operation of the well(s) in the analytical instrument, which is (are) used during the step. Next, the configuration information is downloaded from the database to the analytical instrument. The analytical instrument uses this information to perform the desired test. This is done by causing the analytical instrument to execute the step(s) of the test. Finally, data generated by the test is stored in the database for review, analysis, later retrieval, and so on.

A particularly useful application of these methods and processes is in the analysis of biological samples, as is described herein. Advantages of such a database include the accurate recording of information regarding the test and its protocol, reproducibility of tests, remote access of test protocol and data, and the ability to search network-wide for a given test. For example, a researcher at a given location could access test information stored at a remote location, reproduce the test using local equipment, and verify the results obtained without ever having to contact the party who performed the original test.

A further understanding of the nature and advantages of the invention described herein may be realized by reference to the remaining portions of the specification and the attached drawings.

DESCRIPTION OF THE SPECIFIC EMBODIMENTS

Introduction

A database is described which stores, in a logical and organized fashion, instrumentation settings, results, and other information related to experiments (e.g., assays and other chemical reactions) run on an analytical laboratory instrument. Instrumentation settings may be uploaded to and downloaded from the analytical instrument. Results from experiments may be downloaded to the database, along with instrumentation settings and other information (e.g., date/time, operator, list of reagents, instrument settings, and so on).

The present invention offers several advantages. The experiments carried out on the analytical instrument may be verified easily because all the data necessary to reproduce the experiment is in one place, and is easily accessible because it is in a standard format. Such a database also provides benefits to groups of researchers, allowing them to share results easily, in a format accessible to all of those having the database software, and provides the ability to search for certain experiments based on any number of criteria (e.g., applications, reagents, conditions, results, dates, operator(s), and so on). In a networked environment, this information may be made accessible to colleagues over a company intranet, or even to colleagues at remote locations, using access over an internetwork (e.g., the Internet).

Moreover, access to information stored according to the present invention is extensible. Such a system permits the easy creation of new searches, data views, and so on. Although any analytical instrumentation may be used in conjunction with the present invention, a database according to the present invention is particularly useful in managing a biochemical analysis instrument, capable of performing chemical assays, biochemical assays, biological assays, and similar experiments, although the invention need not be limited to this type of instrument.

A key feature of the present invention is the ability to easily share operating parameters and data over a network, even when the instruments are in different parts of the world. Also important is the reproducibility provided thereby. By downloading the exact parameters used in generating the corresponding data and the results thereof, data generated subsequently can be easily and accurately compared to the data generated originally. In fact, the instrument may be controlled entirely by software using a method according to the present invention. This offers advantages such as remote operation and improved physical security. The present invention also provides the ability to search and manipulate the experimental data thus stored. The present invention may be used, for example, to configure and operate an analytical instrument such as that described infra.

Figure 1:
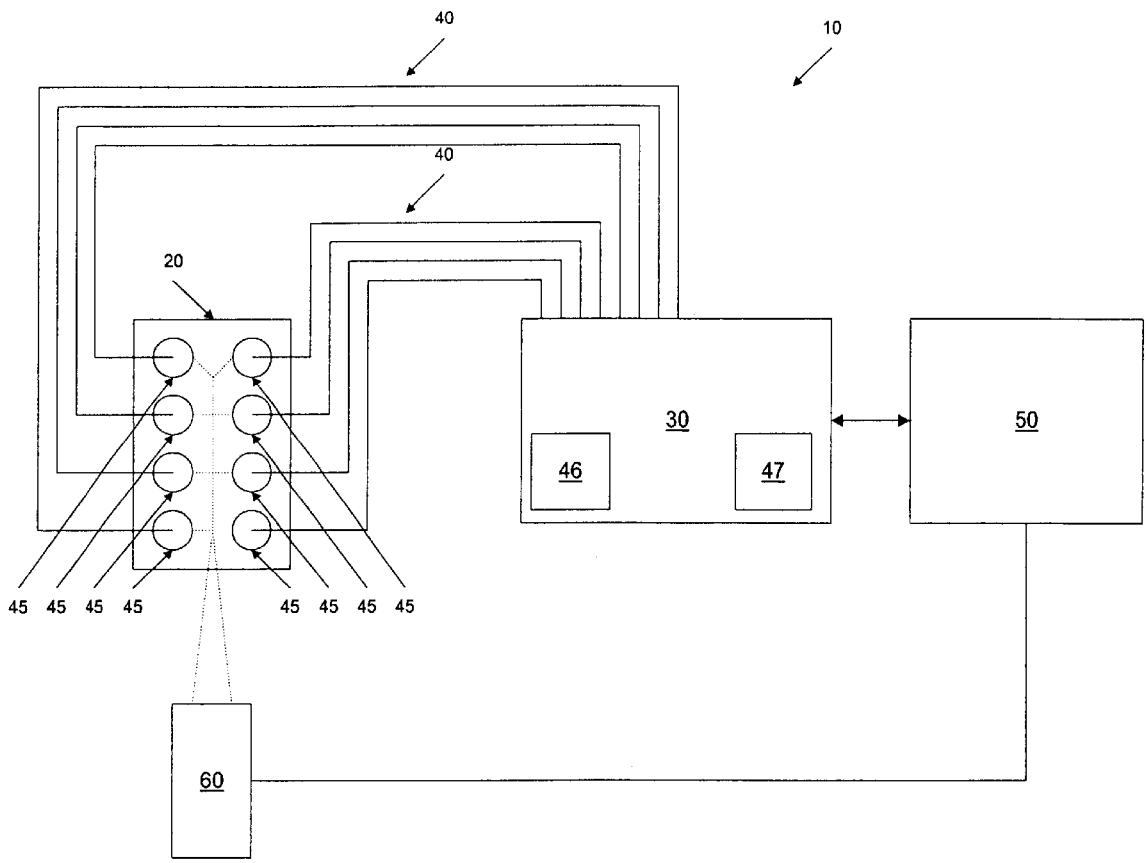
FIG. 1 depicts a control system for electrokinetically moving materials within a microfluidic device.

An Exemplary Analytical Instrument FIG. 1 is a schematic illustration of an analytical instrument 10 capable of carrying out analytical operations using a microfluidic device 20. Microfluidic device 20 employs controlled electrokinetic material transport, as described infra. As shown, microfluidic device 20 is connected to an electrical controller 30 via a series of electrical leads/electrodes 40 Electrodes 40 are disposed in reservoirs 45 that are disposed at the termini of the channels in the channel network within microfluidic device 20. Electrical controller 30 typically includes a power supply 46, as well as control circuitry 47 for regulation of voltage and/or currents applied to each of electrical leads/ electrodes 40 to control material transport, as described infra. One example of such control circuitry is that described in commonly owned Published International Patent Application No. WO 98/00707. The system shown also includes a computer 50, which includes appropriate software or other programming for instructing the electrical controller to apply appropriate voltage/current profiles to the various reservoirs 45 (or channel termini) in order to achieve a desired material movement within the device, e.g., for a given operation. In addition to instructing the electrical controller, the computer also receives data from the controller relating to the electrical parameters within the device, e.g., applied current/voltage, resistance, etc., as well as receiving data from detector 60. For example, in typical applications, detector 60 is preferably an optical, e.g., fluorescence detector, which detects relative fluorescence levels within the device and reports the data to computer 50 for storage and subsequent analysis. Detector 60 is generally disposed adjacent a detection window that is disposed in the device, e.g., a translucent or transparent region of microfluidic device 20. Accordingly, computer 50 is typically programmed to instruct the operation of analytical instrument 10, as well as receive, store, and analyze the data generated by analytical instrument 10. The constituent devices of analytical instrument 10 and their theory of operation are described in greater detail infra.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents, and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays, and detection operations. Assay and detection operations include without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like.

Electrokinetic Material Transport

Analytical instrument 10 employs electrokinetic material transport techniques, and preferably, controlled electrokinetic material transport techniques. As used herein, systems employing such techniques include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode. "Controlled electrokinetic material transport and direction," as used herein, refers to electrokinetic systems as described supra, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes.

In particular, microfluidic device 20 preferably includes a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection.

In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described supra, flow of material from one channel segment to another, e.g., the left arm to the right arm of the horizontal channel, can be efficiently regulated, stopped, and reinitiated, by a controlled flow from the vertical channel, e.g., from the bottom arm to the top arm of the vertical channel. Specifically, in the 'Off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

Microfluidic Device Description

As used herein, the term "microscale" or "microfabricated" generally refers to structural elements or features of a device which have at least one fabricated dimension in the range of from about 0.1 μm to about 500 μm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is substantially within the given dimensions.

In microfluidic device 20, the microscale channels or chambers preferably have at least one cross-sectional dimension are also within the given dimensions. Accordingly, microfluidic device 20 typically includes at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication. The analytical instrument of FIG. 1 (analytical instrument 10) preferably uses a microfluidic device such as that described herein.

The body structure of microfluidic device 20 typically comprises an aggregation of two or more separate layers which when appropriately mated or joined together, form the microfluidic device of the invention, e.g., containing the channels and/or chambers described herein. Typically, microfluidic device 20 will comprise a top portion, a bottom portion, and an interior portion, wherein the interior portion substantially defines the channels and chambers of the device.

A variety of substrate materials may be employed as the bottom portion. Typically, because such devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which microfluidic devices may be exposed, including extremes of pH, temperature, salt concentration, and application of electric fields.

Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described supra, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997 (Attorney Docket No. 17646-002610), and which is incorporated herein by reference in its entirety for all purposes.

Preferably, microfluidic device 20 will include an optical detection window disposed across one or more channels and/or chambers of the device when used in a system such as analytical instrument 10. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing microfluidic device 20, transparent detection windows fabricated from the above materials may be separately manufactured into the device.

Such a microfluidic device allows analytical instrument 10 to perform a variety of functions, including, e.g., the performance of high throughput screening assays in drug discovery, immunoassays, diagnostics, genetic analysis, and the like. As such, microfluidic device 20 will often include multiple sample introduction ports or reservoirs, for the parallel or serial introduction and analysis of multiple samples. Alternatively, the device may be coupled to a sample introduction port, e.g., a pipetor, which serially introduces multiple samples into the device for analysis. Examples of such sample introduction systems are described in e.g., U.S. patent application Ser. Nos. 08/761,575 and 08/760,446 (Attorney Docket Nos. 17646-000410 and 17646-000510, respectively) each of which was filed on Dec. 6, 1996, and is hereby incorporated by reference in its entirety for all purposes.

In analytical instrument 10, for example, such sensors preferably include laser fluorescence devices that detect fluorescence induced by exposure to laser radiation to generate the chromatographic data thus displayed.

Instrumentation

Analytical instrument 10 generally includes one or more microfluidic devices, as described supra, in conjunction with additional instrumentation for controlling fluid transport and direction within the devices (e.g., electrical controller 30), detection instrumentation for detecting or sensing results of the operations performed by the system (e.g., detector 60), one or more processors (e.g., computer 50) for instructing the controlling instrumentation in accordance with preprogrammed instructions, receiving data from the detection instrumentation, and for analyzing, storing, and interpreting the data, and providing the data and interpretations in a readily accessible reporting format.

Controller

A variety of controlling instrumentation (such as electrical controller 30) may be utilized in conjunction with the microfluidic devices described supra, for controlling the transport and direction of fluids and/or materials within the devices of the present invention. For example, in many cases, fluid transport and direction may be controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

Typically, an electrical controller such as electrical controller 30 is employed in analytical instrument to control the flow of materials through microfluidic device 20, and Includes power supply 46 and control circuitry 47 for concurrently delivering appropriate voltages to a plurality of electrodes that are placed in electrical contact with the fluids contained within microfluidic device 20. Examples of particularly preferred electrical controllers include those described in, e.g., U.S. patent application Ser. No. 08/888,064, and International Patent Application No. 97/12930, filed Jul. 2, 1997, the disclosures of which are hereby incorporated herein by reference in their entirety for all purposes.

In brief, such a controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing, and concentrating subject materials and buffer fluids in a complex microfluidic system. Current control is also preferred for moderating undesired temperature effects within the channels.

Detector

In analytical instrument 10, a variety of detection methods and systems may be employed, depending upon the specific operation that is being performed. Often, such a system will employ multiple different detection systems for monitoring the output of the system. Examples of detection systems include optical sensors, temperature sensors, pressure sensors, pH sensors, conductivity sensors, and the like. Each of these types of sensors is readily incorporated into the microfluidic systems described herein. Such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended.

Detector 60 is preferably an optical detection system capable of detecting an optical property of a material within the channels and/or chambers of microfluidic device 20. Such an optical detection system is typically placed adjacent to a microscale channel of microfluidic device 20, and is in sensory communication therewith via an optical detection window disposed across the channel or chamber of the device. Such optical detection systems include systems that are capable of measuring the light emitted from material within the channel, the transmissivity or absorbance of the material, as well as the materials spectral characteristics. In preferred aspects, detector 60 measures an amount of light emitted from the material, such as a fluorescent or chemiluminescent material.

Detector 60 typically includes collection optics for gathering a light based signal transmitted through the detection window, and transmitting that signal to an appropriate light detector. Microscope objectives of varying power, field diameter, and focal length may be readily employed in at least a portion of this optical train. The light detectors may be photodiodes, avalanche photodiodes, photomultinlier tubes, diode arrays, or in some cases, imaging systems, such as charged coupled devices (CCDs) and the like. In preferred aspects, photodiodes are utilized, at least in part, as the light detectors. The detection system is typically coupled to computer 50, via an AD/DA converter, for transmitting detected light data to the computer for analysis, storage, and data manipulation (described in greater detail infra).

In the case of fluorescent materials, detector 60 will typically include a light source which produces light at an appropriate wavelength for activating the fluorescent material, as well as optics for directing the light source through the detection window to the material contained in the channel or chamber. The light source may be any number of light sources that provides the appropriate wavelength, including lasers, laser diodes and LEDs. Other light sources may be required for other detection systems. For example, broadband light sources are typically used in light scattering/transmissivity detection schemes, and the like. Typically, light selection parameters are well known to those of skill in the art.

While it may exist as a separate unit, detector 60 is preferably integrated with electrical controller 30 into a single instrument (as shown in FIG. 1). Integration of these functions into a single unit facilitates connection of these instruments with the computer (described infra), by permitting the use of few or a single communication port(s) for transmitting information between electrical controller 30, detector 60, and computer 50. Moreover, the integration of these components allows the instrument to be controlled completely by the analytical database of the present invention, removing the need for user-accessible controls on the instrument.

Computer

As noted supra, electrical controller 30 and detector 60 are coupled to an appropriately programmed processor or computer (e.g., computer 50) which functions to instruct the operation of these instruments in accordance with preprogrammed or user input instructions, receive data and information from these instruments, and support the interpretation, manipulation, and reporting of this information to the user.

Computer 50 typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate commands for instructing the operation of the fluid direction and transport controller to carry out the desired operation. Computer 50 also receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages/currents, and the like. This control and information flow is the focus of the analytical database of the present invention, as outlined in greater detail infra.

A Remotely-Accessible Database for the Storage and Retrieval of Operating Parameters and Analytical data As noted supra, the methods and processes described herein are particularly useful in analyzing data from microfluidic biochemical analytical systems, such as those described herein. Such systems have a variety of analytical applications, e.g., conventional capillary electrophoresis systems, high-performance liquid chromatography systems, sequencers, molecular array readers, mass spectrometry equipment, and the like.

Figures 2, 3:
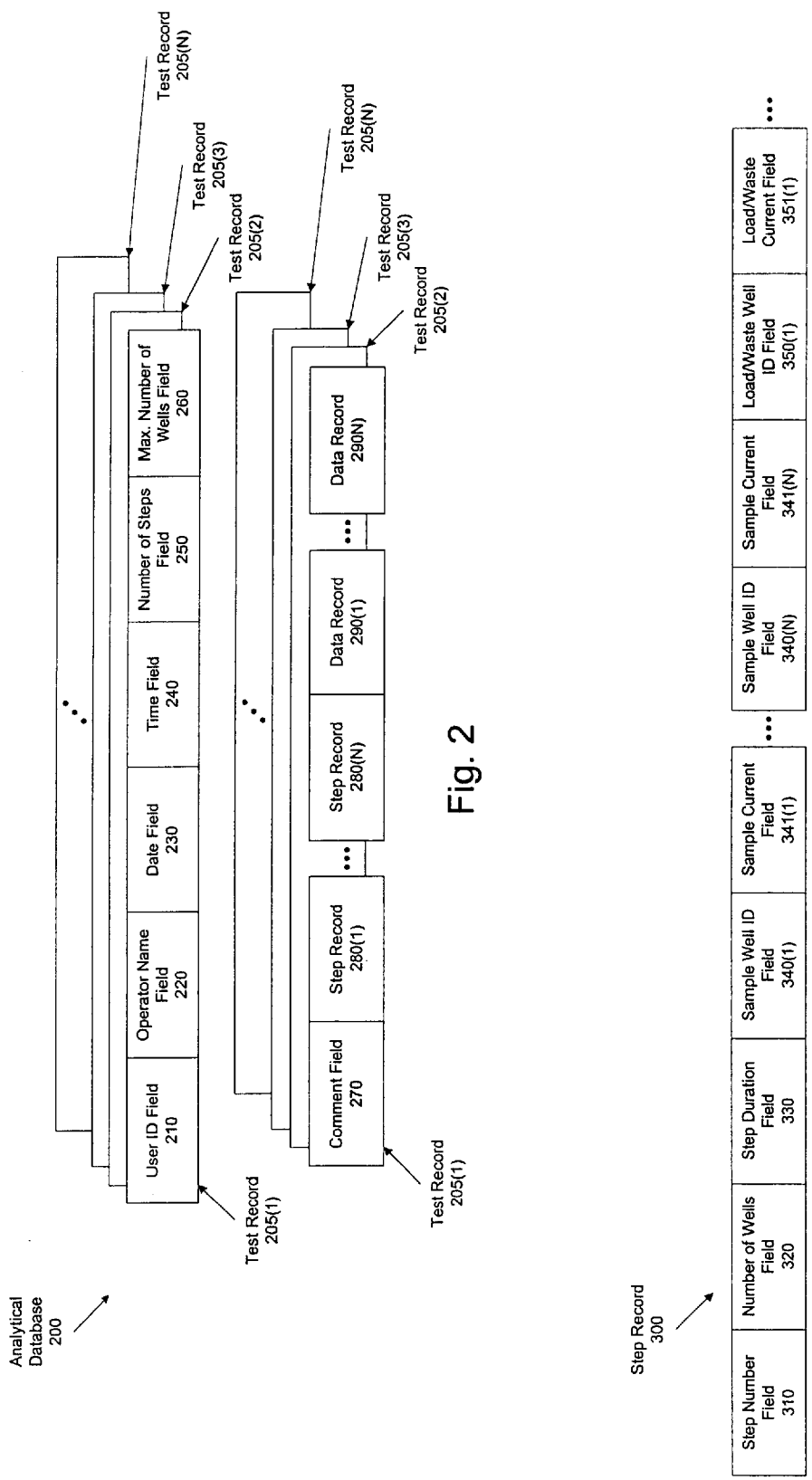
FIG. 2 depicts an analytical database according to one embodiment of the present invention.
FIG. 3 depicts a step record according to one embodiment of the present invention.

FIG. 2 illustrates the basic structure of an analytical database 200 according to the present invention. As with most databases, analytical database 200 is made up of a number of records, test records 205(1)–(N). Other information may be included in analytical database 200, such as generic site information, creation date and time of the database, the database's current size, and so on. This information would not normally be stored in test records 205(1)–(N) because the storage of such information in every test record would be redundant. Thus, most or all of the information common to test records 205(1)–(N) is generally stored in a separate area of analytical database 200.

Each of the test records in analytical database 200 contains similar information. Test record 205(1), for example, is made up of a number of quanta of information arranged in a logical format, such that the storage and retrieval of the information stored therein is both fast and efficient. These quanta of information are commonly known fields and may relate to general information regarding the database, information regarding specific tests recorded therein, information regarding the various steps carried out during these tests, and the like.

Analytical database 200 is shown in FIG. 2 as consisting of several high level fields and records. The high level records include a user identification (ID) field 210, an operator name field 220, a date field 230, a time field 240, the number of steps to be performed in the given test (stored in a number of steps field 250), the maximum number of wells required to perform the given test (stored in a maximum number of wells field 260, which is an indication as to the type of chip to be used in the analytical instrument). It should be noted that one of skill in the art would understand that terms such as "control nodes", "control points", "reagent reservoirs", "points of contact", "chambers", and the like can also be used to describe the "wells" referred to herein. Analytical database 200 also includes fields that are allowed to vary in length, either because the particular field's length cannot be determined beforehand, because it is preferable not to limit the field's length, or because the number of records in the field cannot be determined prior to the test parameters being entered. Such fields include a comment field 270, a variable number of step records (step records 280(1)–(N)), and a variable number of data records (data records 290(1)–(N)). While the database structure shown in FIG. 2 is a preferred structure, other configurations of the information represented therein are possible, and would also provide the benefits of the present invention.

As with any database, each field of analytical database 200 is used to store information necessary to the identification, the performance, or the result of the given test. User ID field 210 contains a unique ID identifying each operator permitted access to analytical database 200. Operator name 220 corresponds to user ID field 210, and holds the name of the operator that corresponds to the user ID. Number of steps field 250 contains the number of steps executed in performing the test represented by a test record in analytical database 200. This field is used to determine the number of records having information therein, and represented by step records 280(1)–(N). This allows the database engine to determine the amount of storage required for the given test.

Maximum number of wells field 260 indicates the maximum number of wells, be they sample wells, load/waste wells, buffer wells, or other types of wells, that will be used during the current test. This information is necessary, in the analytical instrument described previously herein, to ensure that the analytical instrument is configured properly. Comment field 270 is available to the operator to allow textual comments to be made either before or after the test has been performed. Step records 280(1)–(N) represent the parameters used to configure the analytical instrument. Using number of steps field 250, the number of step records can be determined. Data records 290(1)–(N) hold the data generated by the analytical instrument.

A benefit of such a database system is the ability to enforce certain aspects of a test protocol by requiring the entry of information such as that shown in FIG. 2, prior to granting the user access to the analytical instrument. Thus, the user is forced to enter information deemed necessary by the administrators of analytical database 200. For example, a user ID could be required for entry into user ID field 210 of the database. Moreover, information that might otherwise go unrecorded could be entered into analytical database 200 automatically, thereby avoiding entry errors by the operator. For example, once the user ID had been entered, the system could automatically enter the operator name in operator name field 220 by looking up the operator name corresponding to the user ID entered by the operator in a separate database containing such information (although analytical database could be configured to maintain such information). Similarly, date field 230 and time field 240 could be automatically entered by the system upon the creation of a new test record.

FIG. 3 illustrates an exemplary one of step records 280(1)–(N) in further detail, a step record 300. Step record 300 includes some fixed fields and a variable number of parameter fields. Step number field 310 indicates the position of the step with regard to other steps performed during the test. A number of wells field 320 indicates the number of wells that the current step will require. A step duration field 330 indicates the length of time the current step is to be run. The remaining fields indicate which wells are to be used for sample storage, buffer storage, and storage of waste products, and the electrical currents used therewith. In the analytical instrument described subsequently herein, the duration for which an electrical current is applied determines the movement of the given sample or other substance. Thus, these two parameters should be entered for each step, unless default values for these parameters are employed by the analytical instrument being used.

FIG. 3 also illustrates sample well ID fields 340(1)–(N) and sample current fields 341(1)–(N) (i.e., the electrical current applied to the sample well(s)) as the first set of parameter fields in step record 300. Also shown are load/waste well ID field 350(1)–(N), load/waste current field 351(1)–(N) (i.e., the electrical current applied to the load/waste well(s)), buffer well ID fields 360(1)–(N), and buffer current fields 361(1)–(N) (i.e., the electrical current applied to the buffer well(s)). Although the number of wells is limited by the contents of number of wells field 320, each of the well identification and current fields can be used to indicate one of several different configurations for the analytical instrument being controlled. In the analytical instrument described subsequently herein, these fields identify the sources and sinks for various biochemical constituents, and the movement of those constituents through the analytical instrument. Of course, fields storing other parameters, such as material types, voltages, reactant ratios, and the like can easily be envisioned by one of skill in the art.

Figure 4:
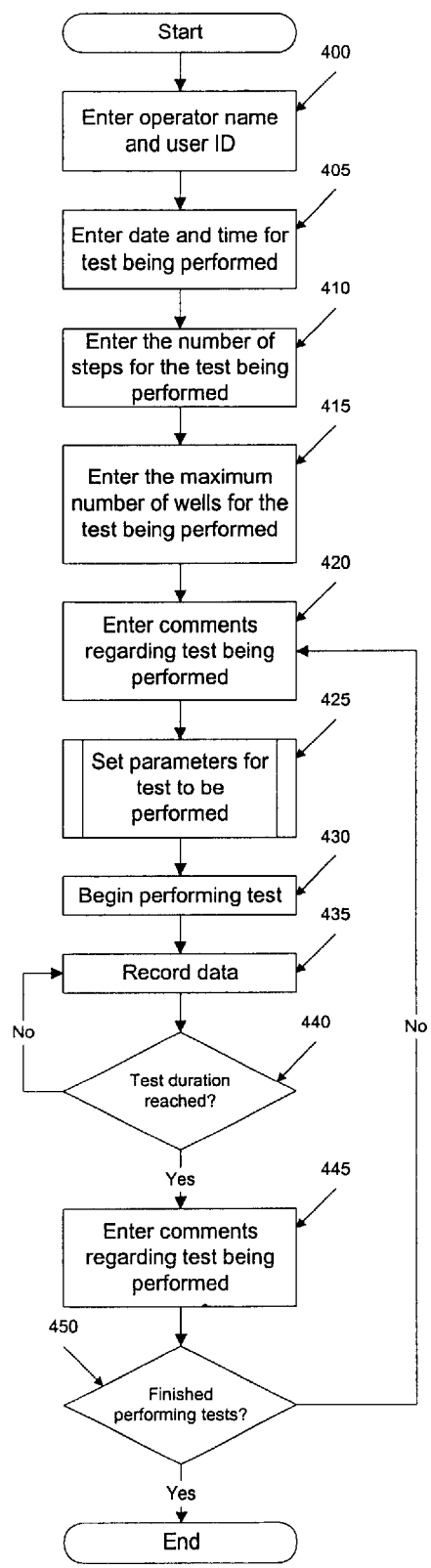
FIG. 4 depicts a flow diagram of one embodiment of the method of the present invention.

FIG. 4 illustrates a process of entering information into a database such as analytical database 200. Such a process begins with the entry of general test information. At step 400, the operator enters his or her name and user ID. As noted, certain information may be automatically entered by the system, such as the operator's name. Next, the current date and time is entered at step 405. As noted, such information may be entered automatically. Next, the number of steps to be performed in completing the current test is entered (step 410). The maximum number of wells for the test being performed is then entered at step 415. Optionally, at step 420, the operator may enter comments regarding the test being performed prior to performing the test. Such comments might include notes describing the suppliers of the biochemicals used, the reasons for performing the test, the hoped for results, and similar information. One skilled in the art will realize that analytical database 200 is easily extended to include certain other information which might be entered as a comment otherwise. Such information might include the make and model of the analytical instrument, environmental parameters, and the like.

At step 425, the parameters for the current test are entered. This process is described in further detail in FIG. 4. At step 430, testing is begun. Data generated by the test is recorded at step 435. This continues until the test is completed (step 440). Alternatively, the data can be recorded at the end of the test. Once the test is completed, the operator may again enter comments regarding the test which has been performed at step 445. Such comments may include notes as to the efficacy of the test, other test results, and the like. This process may be repeated in order to perform further tests (e.g., the tests represented by test records 205(2)–(N)) (step 450).

Figure 5:
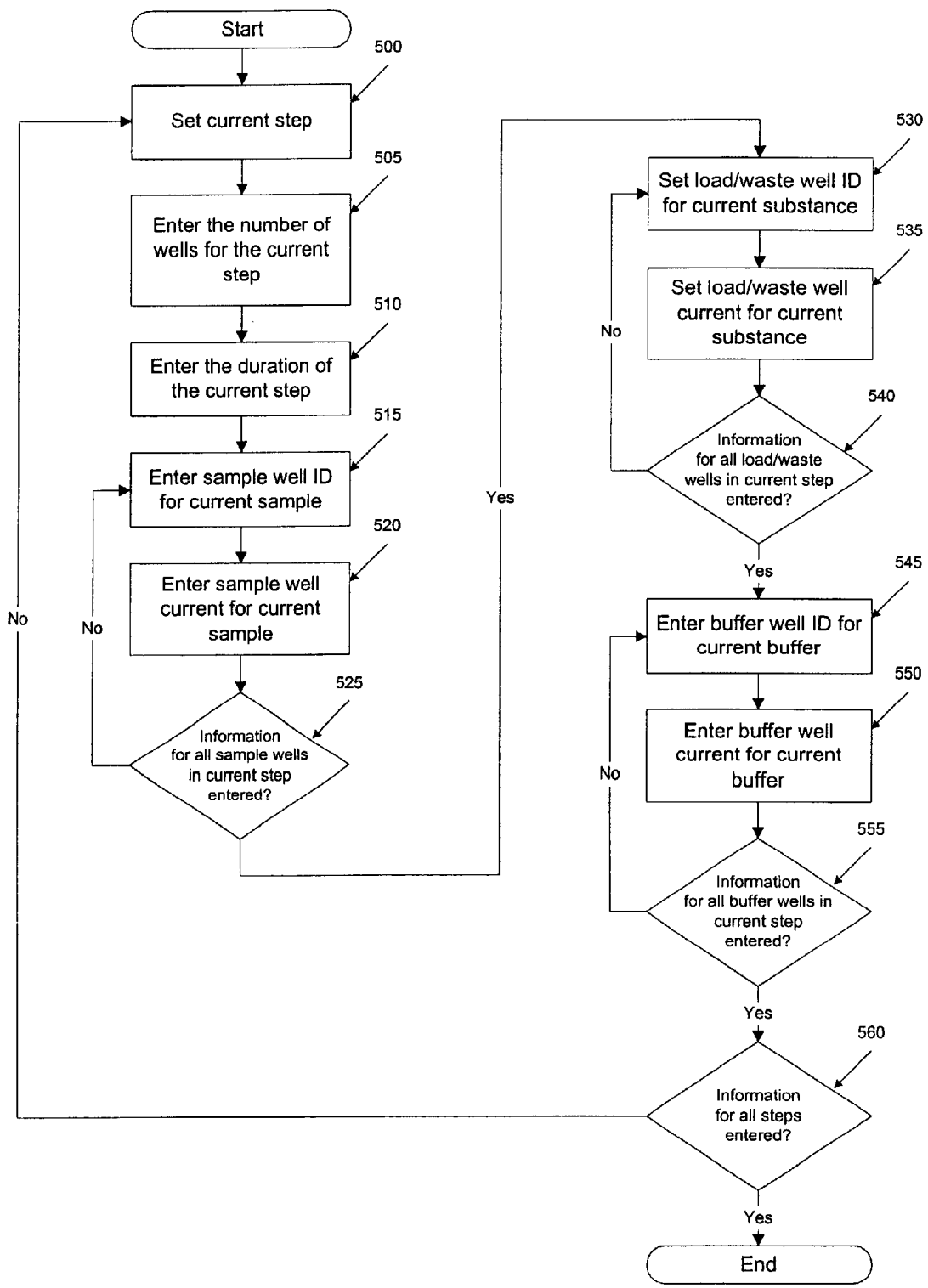
FIG. 5 depicts a flow diagram of the steps performed in setting test parameters in one embodiment of the method of the present invention.

FIG. 5 illustrates step 425 of FIG. 4 in greater detail and in the context of the database architecture illustrated in FIGS. 2 and 3 (i.e., analytical database 200). The process begins at step 500 where the current step number is determined. Next, the number of wells required by the current step is entered (step 505). The duration of the current step is then entered at step 510.

Information regarding the sample wells used in the current step is entered into the database as steps 515–525. At step 515, the sample well ID for the current sample is entered into the database. This information is stored in the current one of sample well ID fields 340(1)–(N). At step 520, the current for this sample well is entered into the database. This indicates the amount of flow from this sample well that is to occur during this step of the test. This information is stored in the current one of sample current fields 341(1)–(N). These steps are repeated until all sample wells in the current step have been entered in analytical database 200 (step 525).

Once the information for all sample wells in the current step has been entered, this process is performed for the load/waste wells used in the current step (steps 530–540). At step 530, the load/waste well ID for the current load/waste substance is entered. This information is stored in the current one of load/waste well ID fields 350(1)–(N). This is followed by entering the current applied to the load/waste well identified in step 530 (step 535). This information is stored in the current one of load/waste current fields 351(1)–(N). These steps are repeated until all load/waste wells in the current step have been entered in analytical database 200 (step 540).

Similar steps are repeated for the buffer wells used in the current step at step 545-555. At step 555, the buffer well ID for the current buffer is entered into analytical database 200. This information is stored in the current one of buffer well ID fields 360(1)–(N). At step 550, the current used to move the buffer from the buffer well identified in step 545 is entered into analytical database 200. This information is stored in the current one of buffer current fields 361(1)–(N). These steps are repeated until all buffer well information for the current step has been entered in analytical database 200 (step 555). The forgoing steps are repeated until the information for each of the steps to be performed in the current test have been entered into analytical database 200 (step 560). Analytical database 200 can be stored on and managed by a computer such as that described infra.

Exemplary Analytical Instrument Architecture

Figure 6:
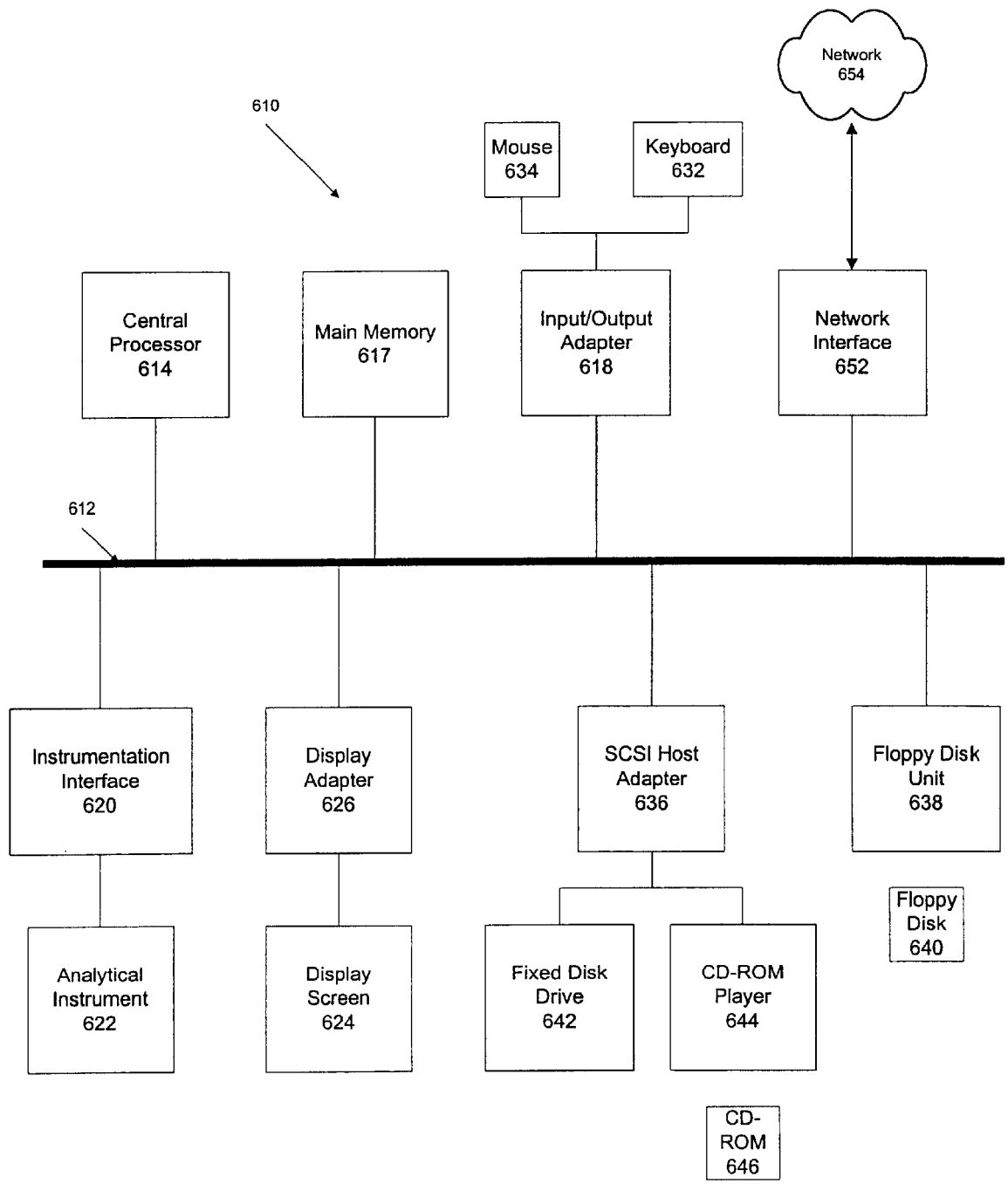
FIG. 6 depicts a computer-controlled analytical instrument according to one embodiment of the present invention.

FIG. 6 illustrates an exemplary analytical instrument architecture. An application according to the present invention is configured to run on a host computer 610, and permit host computer 610 to communicate with one or more other such computers to share instrument settings and data, stored using the method of the present invention, in a networked environment. Host computer system 610 typically is includes a bus 612 which interconnects major subsystems such as a central processing unit (CPU) 614, a system memory 616 (e.g., dynamic random-access memory or DRAM), an input/output (I/O) adapter 618, an external device such as a display screen 624 via display adapter 626, a keyboard 632 and a mouse 634 via I/O adapter 618, and a subsystem controller 636. A floppy disk drive 638 operative to receive a floppy disk 640 is also provided.

Subsystem controller 636 may serve as an interface controller for a fixed disk drive 642 or a CD-ROM player 644, for example. Fixed disk 642 may be a part of computer system 610 or may be separate and accessed through other interface systems (e.g., over a network, as part of a networked filesystem). CD-ROM player 644 is operative to receive a CD-ROM 646. Fixed disk 642 may be a part of host computer 610 or may be separate and accessed through other interface systems. For example, fixed disk 642 can be located in a fileserver accessed by host computer 610 over a local area network. Host computer 610 also includes an instrumentation interface 648 that interfaces host computer 610 to an analytical instrument 650. Instrumentation interface 648 can be a serial or parallel interface, an industry standard interface (e.g., an IEEE-488 General Purpose Instrument Bus (GPIB) interface), or other such interface.

A network interface 652 may also be provided to allow the connection of host computer 610 to a network 654 such as a LAN (e.g., a TCP/IP-based local area network (LAN)) or to an internetwork (e.g., the Internet), for example. Using network 654, host computer 610 is able to send data to network printers (not shown), to send data to and receive data from fileservers, and the like. Many other devices or subsystems (not shown) may be connected in a similar manner. Also, it is not necessary for all of the devices shown in FIG. 6 to be present to practice the present invention, as discussed infra. The configuration of the devices and subsystems shown in FIG. 6 may differ substantially from one computer to the next.

With regard to the present invention, analytical database 200 is normally stored on fixed disk drive 642, but can also be stored on floppy disk 640 or CD-ROM 646, or other storage medium. Normally, a user enters information to be recorded in analytical database 200 using mouse 634 and keyboard 632. However, other means of entering the necessary information (e.g., voice recognition, optical character recognition, and other methods) may be employed. Once this information is entered, the user may choose to store the information on fixed disk 642 (or other media). Interface software is run on host computer 610 to control analytical instrument 650. According to the method of the present invention, host computer 610 causes analytical instrument 650 to execute the desired steps by downloading commands from analytical database 200 to analytical instrument 650 using instrumentation interface 648. This process may include converting information in analytical database 200 into a command format acceptable to one or both of instrumentation interface 648 and analytical instrument 650, if the format in which the control information is stored in analytical database 200 is not compatible with those formats required by instrumentation interface 648 and analytical instrument 650.

Once analytical instrument 650 completes the test in question, data from the test is recorded in analytical database 200 in data records 290(1)–(N). Alternatively, analytical instrument 650, instrumentation interface 648, and host computer 610 can be configured to download data from analytical instrument 650 to analytical database 200 as the data is generated by analytical instrument 650. As previously noted, comments may be entered into analytical database 200 both before and after the test is performed, allowing user comments regarding expected results, actual results, reasons for deviation from expected results, and similar information.

The present invention's ability to centrally record such information provides several benefits, even in a standalone configuration. Tests run using a database system according to the present invention are easier to repeat than without such a database, because of the large number of variables often used in operating analytical instruments (leading to a significant possibility of operator error when manually entering the information during subsequent iterations of the test). Moreover, the entry of vital information such as instrument model number, operating firmware revision number, operator information, environmental parameters, and the like can be mandated, avoiding missing information that can have an effect on test results or make identification of the test difficult. Indeed, the entry of certain information can be automated, not only ensuring that the information is entered correctly, but that the user is required to enter only a minimum of information.

Figure 7:
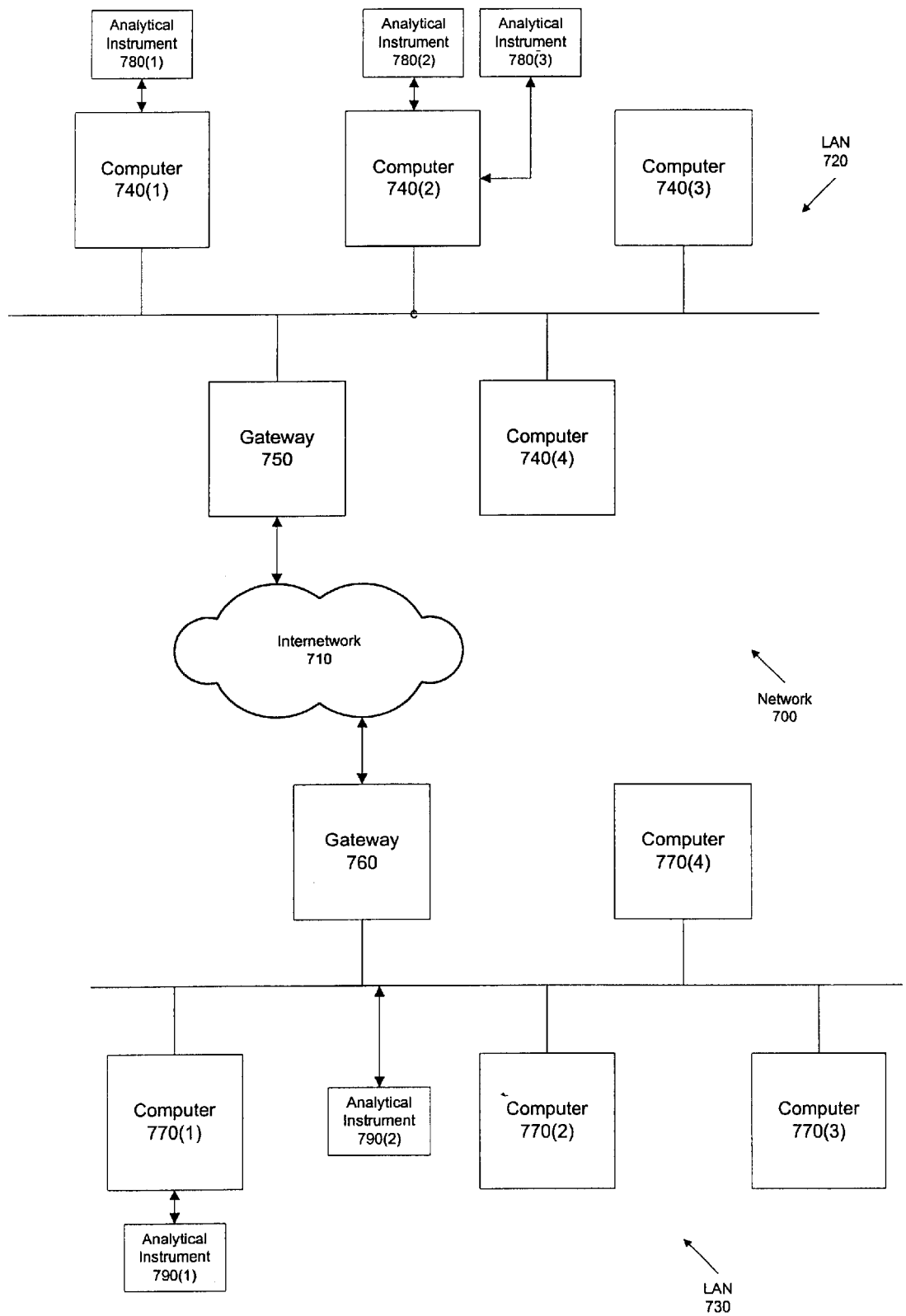
FIG. 7 depicts a network environment according to another embodiment of the present invention.

FIG. 7 illustrates a network 700 that includes an internetwork 710, a local area network (LAN) 720, and a LAN 730. LAN 720 includes computers 740(1)–(4) and provides for the transfer of data files, remote login, and other facilities normally associated with LANs. LAN 720 also includes a gateway 750. Gateway 750 allows computers 740(1)–(4) to access internetwork 710 and other networks that might be attached to internetwork 710. Such a network is exemplified by LAN 730, which is attached to internetwork 710 via a gateway 760 and is accessible thereby. In a similar fashion, gateway 760 allows computers 770(1)–(4) to be accessed by and to access other networks via internetwork 710 (e.g., LAN 720) and computers attached thereto.

Also shown in FIG. 7 are analytical instruments 780(1)–(3) and 790(1)–(2). Analytical instrument 780(1) is connected to computer 740(1), while analytical instruments 780(2) and 780(3) are both connected to computer 740(2). This illustrates that a single computer may control multiple analytical instruments. In a similar fashion, analytical instrument 790(1) is attached to computer 770(1). In order to support analytical instruments 780(1)–(3) and 790(1), computers 740(1)–(2) and computer 770(1) are configured in a manner similar to host computer 510 shown in FIG. 5. Thus, each of these computers possesses hardware and software similar to that illustrated in FIG. 5. In particular, each one of these computers has an instrumentation interface supporting communications with that computer's respective analytical instrument. Additionally, as depicted in FIG. 7, each one of these computers has a network interface coupling that computer to its respective LAN (and so internetwork 710). Alternatively, the analytical instrument may contain a network interface (not shown), allowing access to the instrument by any computer on the LAN to which the instrument is connected. For example, analytical instrument 790(2), having such a network interface, can be accessed by any computer connected to LAN 730, or even by computers connected to LAN 720 (via internetwork 710).

A networked embodiment of the present invention offers several advantages in addition to those offered by a standalone embodiment thereof. One important feature of the present invention is the ability to easily share test parameters and data. For example, such a database provides benefits to groups of researchers, allowing them to share results easily, in a format accessible to all of those having the database software, and provides the ability to search for certain experiments based on any number of criteria (e.g., reagents, conditions, dates, and so on).

Networking support is especially attractive when the instruments are in different parts of the world. Information stored according to the present invention can be shared by researchers having access to a common LAN, or even over an internetwork. For example, information in such a database may be made accessible to colleagues over a company intranet (e.g., LAN 720 or LAN 730), or even to colleagues at remote locations, by permitting access over an internetwork (e.g., internetwork 710 (e.g., the Internet)). The use of security measures would likely be desirable in the latter situation. Further, by downloading the exact parameters used in generating the corresponding data and the results thereof, data generated subsequently can be easily and accurately compared to the data generated originally at a remote location.

The ability to search and manipulate the experimental data thus stored is also an advantage of the present invention. For example, in a network extensible database architecture, all databases that are accessible from a given location on the network can be logically viewed as a single database, and searched. Thus, if any researcher in an organization has performed a test, or generated results, or otherwise entered information matching the search criteria, the user can determine this is the case, identify the requisite information, and retrieve the information. Then, armed with this data, can duplicate the test performed, can alter the test to their specific needs, or otherwise make use of the information, which would otherwise be inaccessible and unknown to them.

Moreover, access to information stored according to the present invention is extensible. Such a system permits the easy creation of new searches, data views, and so on. Although any analytical instrumentation may be used in conjunction with the present invention, the analytical instrument envisioned for use with this database is a biochemical analysis instrument, capable of performing assays and other similar experiments, although the invention need not be limited to this type of instrument.

A database for storing test parameters for and test data from an analytical instrument according to the present invention thus provides greater flexibility in the generation, storage, and retrieval of such data, heretofore unseen in the analytical instrument arena. The invention has now been explained with reference to specific embodiments. Other embodiments will be apparent to those of ordinary skill in the art in view of the foregoing description. It is therefore not intended that this invention be limited except as indicated by the appended claims and their full scope of equivalents. Additionally, one of skill in the art will recognize that, although stated in a specific order in the appended method claims, the steps of a method according to the present invention may be performed in an order other than that presented in those claims.

What is claimed is:

1. A computer-implemented method for operating an analytical instrument, wherein the analytical instrument comprises a plurality of electrical control nodes and is coupled to a computer, said method comprising the steps of:

entering configuration information into a database residing on the computer, wherein said configuration information representing a test performed by the analytical instrument;

downloading said configuration information from said database to the analytical instrument;

performing said test by causing said analytical instrument to execute said test; and storing data generated by said test in said database associated with said test.

2. The computer-implemented method of claim 1, wherein said entering step comprises entering step configuration information for at least one step, said step configuration information representing at least one step performed in executing said test.

3. The computer-implemented method of claim 2, wherein said step configuration information comprises information regarding at least one of the plurality of electrical control nodes, wherein the at least one of the plurality of electrical control nodes is used during said at least one step.

4. The computer-implemented method of claim 2, wherein said step configuration information comprises:

sample well information;

load/waste well information; and buffer well information.

5. The computer-implemented method of claim 4, wherein said sample well information comprises:

sample well identification information; and electrical current information for a sample well identified by said sample well identification information.

6. The computer-implemented method of claim 4, wherein said load/waste well information comprises:

load/waste well identification information; and electrical current information for a load/waste well identified by said load/waste well identification information.

7. The computer-implemented method of claim 4, wherein said buffer well information comprises:

buffer well identification information; and electrical current information for a buffer well identified by said buffer well identification information.

8. A computer system comprising:

a storage device for storing a database;

a processing system coupled to said storage device, wherein said processing system is configured to operate an analytical instrument, said analytical instrument comprising a plurality of electrical control nodes, by virtue of being configured to:

store configuration information in said database, wherein:

said configuration information comprises step configuration information representing at least one step performed in executing a test to be performed by the analytical instrument, and said step configuration information comprises information regarding at least one of said plurality of electrical control nodes, said at least one of said plurality of electrical control nodes being used during said at least one step;

download said configuration information from said database to the analytical instrument;

perform said test by causing said analytical instrument to execute said at least one step; and store data generated by said test in said database associated with said test.

9. The computer system of claim 8, wherein said processing system is coupled to said analytical instrument by a dedicated interface module.

10. The computer system of claim 8, wherein said processing system is coupled to said analytical instrument by a network.

11. The computer system of claim 8, wherein said processing system is coupled to a second analytical instrument.

12. The computer system of claim 8, wherein said step configuration information comprises:

sample well information;

load/waste well information; and buffer well information.

13. The computer system of claim 12, wherein said sample well information comprises:

sample well identification information; and electrical current information for a sample well identified by said sample well identification information.

14. The computer system of claim 12, wherein said load/waste well information comprises:

load/waste well identification information; and electrical current information for a load/waste well identified by said load/waste well identification information.

15. The computer system of claim 12, wherein said buffer well information comprises:

buffer well identification information; and electrical current information for a buffer well identified by said buffer well identification information.

16. A computer program product for operating an analytical instrument, wherein the analytical instrument comprises a plurality of electrical control nodes and is coupled to a computer, said product comprising:

code that stores configuration information into a database stored on the computer, said configuration information representing a test to be performed by the analytical instrument;

code that downloads said configuration information from said database to the analytical instrument;

code that causes said analytical instrument to perform said test;

code that stores data generated by said test in said database associated with said test; and a computer-readable medium that stores said codes.

17. The computer program product of claim 16, wherein:

said configuration information comprises step configuration information representing at least one step performed in executing said test, and said step configuration information comprises information regarding at least one of the plurality of electrical control nodes, the at least one of the plurality of electrical control nodes being used during said at least one step.

18. The computer program product of claim 17, wherein said step configuration information comprises:

sample well information;

load/waste well information; and buffer well information.

19. The computer program product of claim 18, wherein said sample well information comprises:

sample well identification information; and electrical current information for a sample well identified by said sample well identification information.

20. The computer program product of claim 18, wherein said load/waste well information comprises:

load/waste well identification information; and electrical current information for a load/waste well identified by said load/waste well identification information.

21. The computer program product of claim 18, wherein said buffer well information comprises:

buffer well identification information; and electrical current information for a buffer well identified by said buffer well identification information.

22. A computer system comprising:

a storage device for storing a database;

a first analytical instrument, said first analytical instrument having a plurality of electrical control nodes;

a processing system coupled to said storage device and said first analytical instrument, wherein said processing system is configured to operate said first analytical instrument by virtue of being configured to:

store configuration information in said database, wherein:

said configuration information comprises step configuration information representing at least one step performed in executing a test to be performed by said first analytical instrument, and said step configuration information comprises information regarding at least one of said plurality of electrical control nodes, said at least one of the plurality of electrical control nodes being used during said at least one step;

download said configuration information from said database to said first analytical instrument;

perform said test using said first analytical instrument by causing said first analytical instrument to execute said test by executing said at least one step; and store data generated by said test in said database associated with said test.

23. The computer system of claim 22, wherein said processing system is coupled to a second analytical instrument and said processing system is configured to operate said second analytical instrument by virtue of being configured to:

download said configuration information from said database to said second analytical instrument;

perform said test using said second analytical instrument by causing said second analytical instrument to execute said test by executing said at least one step; and store data generated by said test in said database.

24. The computer system of claim 23, wherein said processing system is coupled to said first and said second analytical instruments by a network.

25. The computer system of claim 24, wherein said processing system is configured to permit the comparison of data generated by said first analytical instrument with data generated by said second analytical instrument.

26. The computer system of claim 24, wherein said processing system is configured to download configuration information to said first analytical instrument and said second analytical instrument.

27. An analytical system, comprising:

a microfluidic device having a plurality of electrical control nodes operably coupled to an integrated channel network disposed in said microfluidic device;

an electrical controller operably coupled to said plurality of electrical control nodes, said electrical controller configured to transmit a first plurality of electrical signals to said plurality of electrical control nodes and receive a second plurality of electrical signals from said plurality of electrical control nodes; and a database stored on a storage device, said database configured to store in association a first dataset representing said first plurality of electrical signals and a second dataset representing said second plurality of electrical signals, wherein said first dataset represents an analytical function to be performed by said analytical system, said second dataset represents results of said analytical function performed by said analytical system, and said storage device is coupled to a computer.

* * * * *

UNITED STATES PATENT AND TRADEMARK OFFICE
CERTIFICATE OF CORRECTION

PATENT NO. : 6,366,924 B1  
APPLICATION NO. : 09/123022  
DATED : April 2, 2002  
INVENTOR(S) : J. Wallace Parce Page 1 of 1

It is certified that error appears in the above-identified patent and that said Letters Patent is hereby corrected as shown below:

Column 16, Line 30 Claim 1
Please change "representing" to --represents--.

Signed and Sealed this
Twenty-eighth Day of June, 2011

David J. Kappos
*Director of the United States Patent and Trademark Office*